US008197529B2

(12) United States Patent
Cully et al.

(10) Patent No.: US 8,197,529 B2
(45) Date of Patent: Jun. 12, 2012

(54) REMOVABLE STENT-GRAFT

(75) Inventors: Edward H. Cully, Flagstaff, AZ (US);
Erin B. Hutchinson, Parks, AZ (US);
Michael J. Vonesh, Flagstaff, AZ (US);
Woodrow W. Watson, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 282 days.

(21) Appl. No.: 12/491,895

(22) Filed: Jun. 25, 2009

(65) Prior Publication Data
US 2009/0259294 A1 Oct. 15, 2009

Related U.S. Application Data

(63) Continuation of application No. 10/737,324, filed on Dec. 16, 2003, now abandoned.

(51) Int. Cl.
*A61F 2/06* (2006.01)

(52) U.S. Cl. .................................................... 623/1.13

(58) Field of Classification Search .......... 623/1.1–1.15, 623/1.22, 1.23, 1.3, 1.36, 23.64, 23.66, 23.69, 623/23.7; 606/191–195
See application file for complete search history.

(56) References Cited

U.S. PATENT DOCUMENTS

| | | |
|---|---|---|
| 3,953,566 A | 4/1976 | Gore |
| 3,993,078 A | 11/1976 | Bergentz et al. |
| 4,503,569 A | 3/1985 | Dotter |
| 4,512,338 A | 4/1985 | Balko et al. |
| 4,553,545 A | 11/1985 | Maass et al. |
| 4,655,771 A | 4/1987 | Wallsten |
| 4,790,809 A | 12/1988 | Kuntz |
| 4,998,539 A | 3/1991 | Delsanti |
| 5,037,427 A | 8/1991 | Harada et al. |
| 5,104,388 A | 4/1992 | Quackenbush |
| 5,226,913 A | 7/1993 | Pinchuk |
| 5,324,304 A | 6/1994 | Rasmussen |
| 5,411,549 A | 5/1995 | Peters |
| 5,443,496 A | 8/1995 | Schwartz et al. |
| 5,474,563 A | 12/1995 | Myler et al. |

(Continued)

FOREIGN PATENT DOCUMENTS

EP 0 237 021 3/1986

(Continued)

*Primary Examiner* — William H. Matthews
(74) *Attorney, Agent, or Firm* — Andrea W. Burke

(57) ABSTRACT

A removable device such as a stent-graft, intended for applications where it may be desirable to remove the device at some time following implantation. The stent-graft of the present invention includes a helically-wound stent component provided with a covering of graft material. It is removable by gripping an end of the helically-wound stent component with a retrieval device and applying tension to the stent component in the direction in which it is intended to be withdrawn from the site of implantation. The use of such a retrieval device allows the stent-graft to be removed remotely, such as via a catheter inserted into the body at a different location from the implantation site. The design of the stent-graft is such that the stent component is extended axially while the adjacent portion of the graft separates between windings of the stent component. The axial extension of the stent component, with portions of the graft still joined to the stent component, allows the device to be "unraveled" (or "unwound") and removed through a catheter of diameter adequately small to be inserted into the body cavity that contained the stent-graft. It is removed atraumatically, without incurring significant trauma to the body conduit in which it had been deployed.

14 Claims, 8 Drawing Sheets

U.S. PATENT DOCUMENTS

| | | | |
|---|---|---|---|
| 5,476,589 | A | 12/1995 | Bacino |
| 5,514,176 | A | 5/1996 | Bosley, Jr. |
| 5,531,788 | A | 7/1996 | Dibie et al. |
| 5,540,701 | A | 7/1996 | Sharkey et al. |
| 5,628,788 | A | 5/1997 | Pinchuk |
| 5,735,892 | A | 4/1998 | Myers et al. |
| 5,782,903 | A | 7/1998 | Wiktor |
| 5,799,384 | A | 9/1998 | Schwartz et al. |
| 5,800,526 | A | 9/1998 | Anderson et al. |
| 5,814,063 | A | 9/1998 | Freitag |
| 5,833,707 | A | 11/1998 | McIntyre et al. |
| 5,876,432 | A | 3/1999 | Lau et al. |
| 5,893,868 | A | 4/1999 | Hanson et al. |
| 6,090,115 | A | 7/2000 | Beyar et al. |
| 6,159,565 | A | 12/2000 | Campbell et al. |
| 6,165,217 | A | 12/2000 | Hayes |
| 6,171,338 | B1 | 1/2001 | Talja et al. |
| 6,258,117 | B1 | 7/2001 | Camrud et al. |
| 6,315,792 | B1 | 11/2001 | Armstrong et al. |
| 6,350,277 | B1 | 2/2002 | Kocur |
| 6,352,561 | B1 | 3/2002 | Leopold et al. |
| 6,364,904 | B1 | 4/2002 | Smith |
| 6,485,513 | B1 | 11/2002 | Fan |
| 6,494,908 | B1 | 12/2002 | Huxel et al. |
| 6,551,350 | B1 | 4/2003 | Thornton et al. |
| 6,629,350 | B2 | 10/2003 | Motsenbocker |
| 6,629,992 | B2 | 10/2003 | Bigus |
| 6,790,226 | B2 | 9/2004 | Edwin et al. |
| 6,827,731 | B2 | 12/2004 | Armstrong et al. |
| 7,914,568 | B2 * | 3/2011 | Cully et al. .................. 623/1.13 |
| 2001/0003801 | A1 | 6/2001 | Strecker |
| 2002/0040236 | A1 | 4/2002 | Lau et al. |
| 2003/0024534 | A1 | 2/2003 | Silvestri et al. |
| 2003/0114922 | A1 | 6/2003 | Iwasaka et al. |
| 2004/0093065 | A1 | 5/2004 | Yachia et al. |
| 2004/0116996 | A1 | 6/2004 | Freitag |
| 2004/0167635 | A1 | 8/2004 | Yachia et al. |
| 2005/0131423 | A1 | 6/2005 | Yachia et al. |

FOREIGN PATENT DOCUMENTS

| | | |
|---|---|---|
| EP | 364420 | 4/1990 |
| EP | 423916 | 4/1991 |
| EP | 1 110 561 | 6/2001 |
| WO | 95/05131 | 2/1995 |
| WO | 96/21404 | 7/1996 |
| WO | WO 97/21403 | 6/1997 |
| WO | 00/42949 | 7/2000 |
| WO | 02/083037 | 10/2002 |
| WO | 03/099166 | 12/2003 |
| WO | 06/036912 | 4/2006 |

\* cited by examiner

REMOVABLE STENT-GRAFT

CROSS REFERENCE TO RELATED APPLICATIONS

This application is a continuation of U.S. patent application Ser. No. 10/737,324 filed Dec. 16, 2003, now abandoned.

FIELD OF THE INVENTION

The present invention relates to the field of removable stent-grafts.

BACKGROUND OF THE INVENTION

Endoluminal stenting has provided a major advancement in clinical treatment modalities offering a significant reduction in perioperative treatment times, iatrogenic injury, postoperative morbidity and healing times. Even with the unprecedented clinical advantages of these devices, there still remains a number of limitations and disadvantages of the technologies currently available. The two primary technologies available for endoluminal stenting are the use of bare metal stents and stent devices provided with a covering or lining of a tubular graft material, i.e., stent-grafts. Either of these technologies may be made to be deployed via inflation of a catheter balloon (e.g., stainless steel stents) or to be self-expanding (e.g., nitinol stents). All of these technologies exhibit a common disadvantage in that none of the commercially available devices are designed to be removable after implantation.

There are numerous applications for which a removable stent-graft would be highly desirable. Even though great strides have been undertaken to enhance biocompatibility of these devices, it is still a synthetic, non-living tissue device that constitutes a foreign body. As a result, living tissue has a number of limitations and/or reactions in coping with such a foreign body.

The most common of these is infection. Typically, when a synthetic device becomes infected, or colonized by bacteria, there is little success in resolving such an infected device or infected area short of device removal from the patient. In some instances, if an infected synthetic device cannot be removed enabling the antibiotic treatment of the affected living tissue, patient mortality can result due to septic shock.

Another issue associated with implantation of endoluminal stents and stent-grafts is foreign body reaction. Endoluminal stents and stent-grafts are often employed to limit, or control, the body's normal healing response (restenosis) to vascular, luminal, or ductal injury due to balloon dilatation. Even though these devices aid in limiting the amount of restenosis as a result of vessel or ductal injury, after a period of time the vessel or duct may generate a hyperplastic tissue (restenotic) or calcific stone formation response due to the presence of the foreign body. Consequently, removal of the device after the appropriate therapeutic period may be desirable.

Still another application for a removable stent-graft would involve providing a removable support structure for delivery of certain other implantable materials or structures (e.g., tubular structures) which otherwise do not exhibit the necessary mechanical characteristics for device delivery without the aid of a temporary, supporting stent component.

Further, mechanisms for localized drug delivery continue to be a highly sought after treatment option which offer many advantages over systemic drug delivery. Two of the key challenges in local drug delivery are the delivery mechanism and the drug elution profile or therapeutic window of the drug delivery. These are not unusually interrelated. By employing one or more applications of a removable drug eluting stent-graft, therapeutic windows can be greatly increased providing unlimited drug application profiles.

Thus, the array of clinical treatments modalities for such a removable endoluminal stent-graft includes: malignant and benign strictures of the biliary tract due to tumor compression, anastomotic and bile stone nidus; anastomotic and benign strictures of the colon, small intestine and ureter/urethra; esophagus collapse syndrome and gastric reflux erosion; strictures of the tracheal/bronchial tree; treatment of vascular disease or injury; and localized drug delivery for various chemotherapy application.

Various designs for removable stents are known in the art. For example, Myler et al. in U.S. Pat. No. 5,474,563 describe a retrievable stent and retrieval tool. The described stent is removed intact, at its fully deployed dimensions, and may consequently pose a risk of trauma during removal.

U.S. Pat. No. 5,782,903 to Wiktor et al. describes a removable stent system which comprises a continuous serpentine wire formed into helical coil. The coil after implantation can be uncoiled by use of a retrieval line. Beyar et al. in U.S. Pat. No. 6,090,115 also describe a temporary stent system comprising a stent constructed of a helical coil of biocompatible material. Both of these references teach that the stent is not covered (i.e., is not a stent-graft) and therefore provides opportunity for tissue in-growth into the spaces between the coil structure over time. This in-growth may result in trauma to the implant site during retrieval.

U.S. Pat. No. 5,799,384 to Schwartz et al. teaches a stent similar to the above-described Wiktor et al. stent. It differs from the Wiktor et al. stent in that a tape of polymeric film is provided to the stent wire, the length of the tape running parallel to the length of the wire with the width of the tape being centered over the stent wire and therefore extending perpendicularly from the stent wire a short distance from both sides of the wire. When the wire is wound into a helical form to create a stent structure, the polymeric tape provides a sort of graft covering. However, this graft covering is discontinuous and therefore cannot offer the advantages of a continuous graft covering extending for all or a major portion of the length of the implantable stent structure.

Huxel et al. in U.S. Pat. No. 6,494,908 describe a removable stent in the form of a helical winding wherein adjacent windings are in direct contact; removal is accomplished by grasping an end of the helix and unwinding the helical form. The helical form of the Huxel et al. device is made from a soft, flexible fiber that is provided with an outer coating of a bioabsorbable material to render it rigid for insertion into a body conduit. The device becomes thinner and flexible over time in order to allow the stent to be removable after a predetermined time has passed. U.S. Pat. No. 5,514,176 to Bosley et al. teaches a somewhat similar device in the form of a removable stent-graft made from a series of helical windings with the adjacent windings in contact with each other. An exterior coating of silicone is provided to seal between the adjacent windings. Removal is accomplished by unwinding the device whereby the coating is removed simultaneously with the helical winding.

Camrud et al., in U.S. Pat. No. 6,258,117, teach a multi-section stent which incorporates a connecting structure that can separate. This ability to separate adjacent segments of the connecting structure however is promoted as a means to add flexibility to the implanted device rather than as a way to atraumatically remove portions of it. Removability of the segments is not taught or suggested. Iwasaka et al. in US Patent Application Publication No. 2003/0114922 describe a stent-graft having a series of discrete, ring-like stent structures along its length. The device is removed from a body conduit by grasping its distal end with a retrieval device and everting it from the distal end by pulling it through itself in a proximal direction. The device is removed in its entirety rather than being removed segmentally.

WO00/42949 teaches the construction of an impermeable stent-graft that is primarily intended for biliary applications. This stent-graft is not described as being removable.

SUMMARY OF THE INVENTION

The present invention relates to removable, implantable devices such as removable stent-grafts or removable filter devices (e.g., embolic filters or vena cava filters). Such devices are intended for applications wherein it may be deemed necessary to remove the device at some time following implantation. Such applications may include stent-grafts for implantation in urethras, in biliary ducts, in the vascular system, the large or small intestine, or in the esophagus or trachea. It may be desirable for a stent-graft to be removable in applications where the stent-graft has been inserted to prevent obstruction of a duct by anastomotic stricture or by a tumor, particularly prior to determining if the tumor is malignant or benign. It may be desirable for such a stent-graft to be removable if its intended purpose was temporary, such as for delivery of a therapeutic agent such as drugs or radioactive materials to a specific site for a limited time. It may be also be of value to enable the stent-graft to be removed in the event that it does not effect its intended purpose and must be replaced by another device.

Devices of the present invention comprise a structural support, such as a stent component, provided with a covering of a graft material. Adjacent elements of the structural support are spaced apart, i.e., not in continuous direct contact with each other when the device is in a relaxed state without any deforming force applied to it. The covering graft material generally extends between the ends of the device and covers the spaces between the adjacent elements of the structural support.

The stent-graft of the present invention has a continuous luminal surface, meaning that, prior to removal, the graft material covering the stent component extends in a substantially continuous fashion between the opposing ends of the device. While the graft material may be separable between adjacent windings of the stent component during removal (as by splitting or tearing) as will be further described, the graft material is substantially integral prior to removal and does not include gaps between adjacent windings of the stent component (as shown by, for example, U.S. Pat. No. 5,799,384) prior to removal. The continuous luminal surface does not preclude the possibility of openings through portions of the graft material at desired locations for purposes of the particular stent application.

The graft material covering the stent component may be provided on the exterior surface of the stent component, the luminal surface of the stent component, or may cover both the exterior and luminal surfaces.

The device of the present invention is removable by gripping an end of the helically-wound structural support with a retrieval device and applying tension to the structural support in the direction in which it is intended to be withdrawn from the site of implantation. The design of the device is such that the structural support (e.g., stent component) is extended axially while the adjacent portion of the graft separates between windings of the structural support. For a stent-graft, for example, the axial extension of the stent component, with adjacent portions of the graft still joined to the stent component, allows the device to be "unraveled" (or "unwound") and removed through a catheter of diameter adequately small to be inserted into the body cavity that contained the previously-deployed stent-graft.

The stent-graft is cohesively removable (i.e., is cohesively disassembled), meaning that it is removed in its entirety, without loss of pieces or the formation of separate remnants during the removal (e.g., the unraveling) process.

The stent-graft is remotely removable, in that it may be grasped at one end for removal by a retrieval device inserted from a more distant point of entry into a body. Further, the removal is substantially or entirely atraumatic to the body conduit in which the device had been originally deployed. This is because the unravelable stent graft lends itself to removal with minimal force and to being removed through a relatively small diameter catheter.

This "unravelable" stent component may also enable the delivery of an intraluminal graft to an intended site and deployment of the intraluminal graft securely against the luminal surface of that site. Following deployment, the stent component may be removed (simultaneously with the delivery system, or alternatively, separately removed at a later time), leaving the graft component implanted at the site.

In still another embodiment, the stent-graft of the present invention may be delivered and deployed at a desired site, with permanently attached but separate stent components also deployed and intended to be left implanted permanently at, for example, the ends of the stent-graft. Another stent component extending along the remaining length of the device not supported by the permanent stent components may then be removed following successful deployment and implantation. This temporary stent component may be useful, for example, to assure that the device is implanted without twisting or other misalignment, and thus removed once it has served its temporary purpose.

Still further, the stent-graft or the stent component thereof may be made to be removable in lengthwise sections or segments.

The stent component is preferably metallic and more preferably is stainless steel or nitinol. It may be balloon expandable or self-expanding. The graft material that covers the stent component may be of a variety of implantable materials such as nylon, polyethylene terephthalate or polytetrafluoroethylene, and is preferably of expanded polytetrafluoroethylene (ePTFE) made as taught by U.S. Pat. No. 3,953,566 to Gore. Alternatively, either or both of the stent component and the graft component may be made of any of a variety of resorbable materials. These resorbable materials may optionally be used in combination with various non-resorbable materials for particular applications as desired.

DETAILED DESCRIPTION OF THE INVENTION

Figure 1:
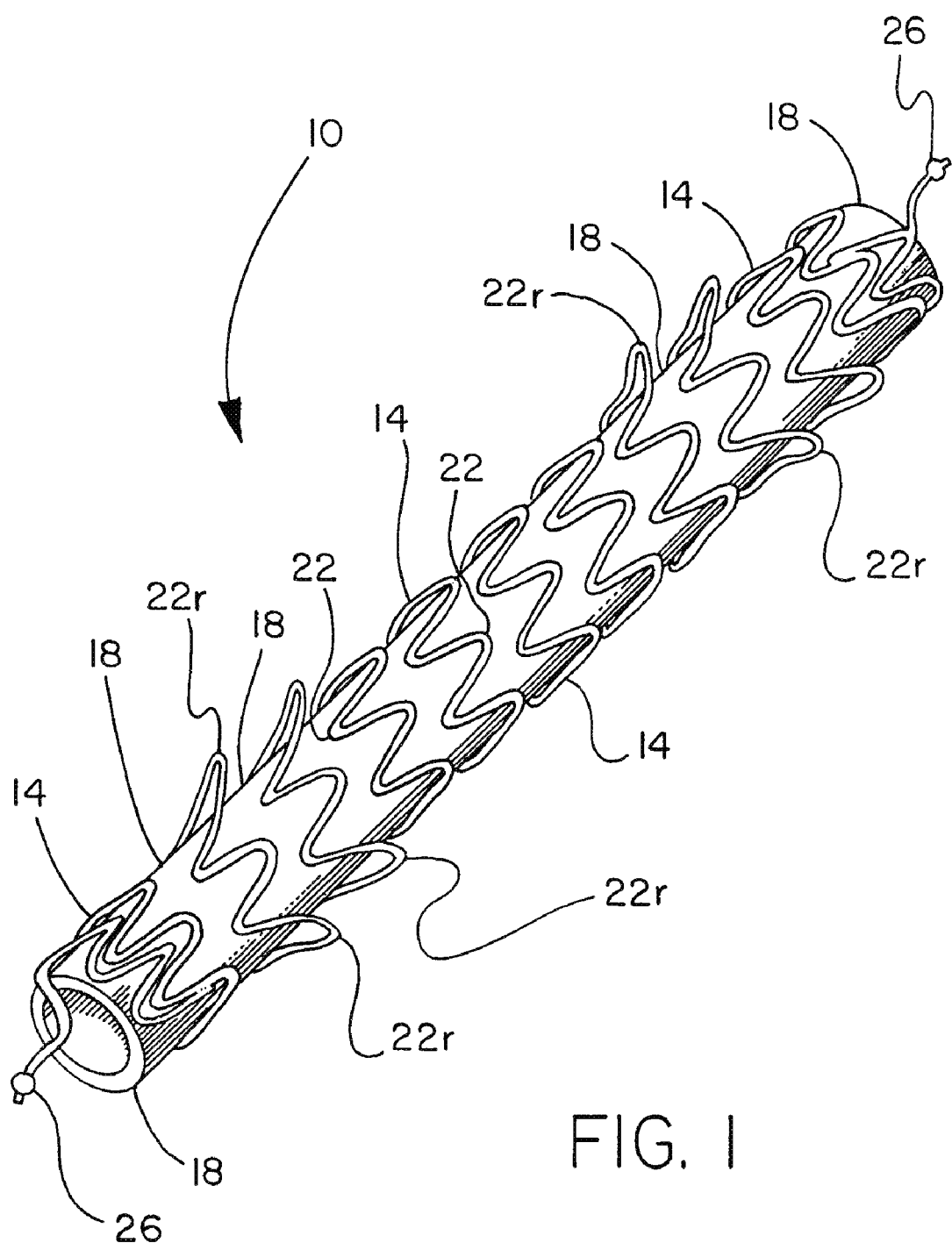
FIGS. 1 and 1A are perspective views of stent-grafts of the present invention showing the stent component provided with a thin, flexible covering of graft material.

FIG. 1 is a perspective view of the device 10 of the present invention wherein the device is composed of a structural component such as stent component 14, provided with a thin, flexible covering of graft material 18. The graft material 18 can be either impermeable or permeable depending upon the needs of the application. An impermeable material would prevent the transmission of fluids and/or cells, such as bile and/or tumor or epithelial cells, through the graft material while a permeable material would allow the transmission of fluids through the graft material. It is also possible to laminate one or more layers of a porous or permeable material to one or more layers of impermeable material. This may be done, for example, where the porous material is desired to provide for tissue attachment to one or both surfaces, while simultaneously providing a construction that is fluid impermeable through its thickness. Generally, impermeable coverings are preferred for biliary applications or applications wherein it is desired to inhibit or preclude cellular ingrowth.

In the embodiment shown by FIG. 1, the stent component 14 comprises wire which has been formed into a serpentine shape having apices 22, which shape is also helically wound into a tubular form. The radii of the apices 22 of the serpentine shape can be as large or small as desired for an intended application. Minimal radii result in the serpentine shape having relatively pointed apices 22, i.e., a zig-zag form. Attached to the wire at the ends are engagement fittings 26, which extend from either or both ends of the device 10. These engagement fittings 26 may be grasped by or attached to a surgical instrument to provide for removing (e.g., by cohesively disassembling) the device 10 during remote atraumatic removal of device 10 from a patient in situ through a small diameter working catheter or sheath. Removal of device 10 will be described in further detail.

Figure 1A:
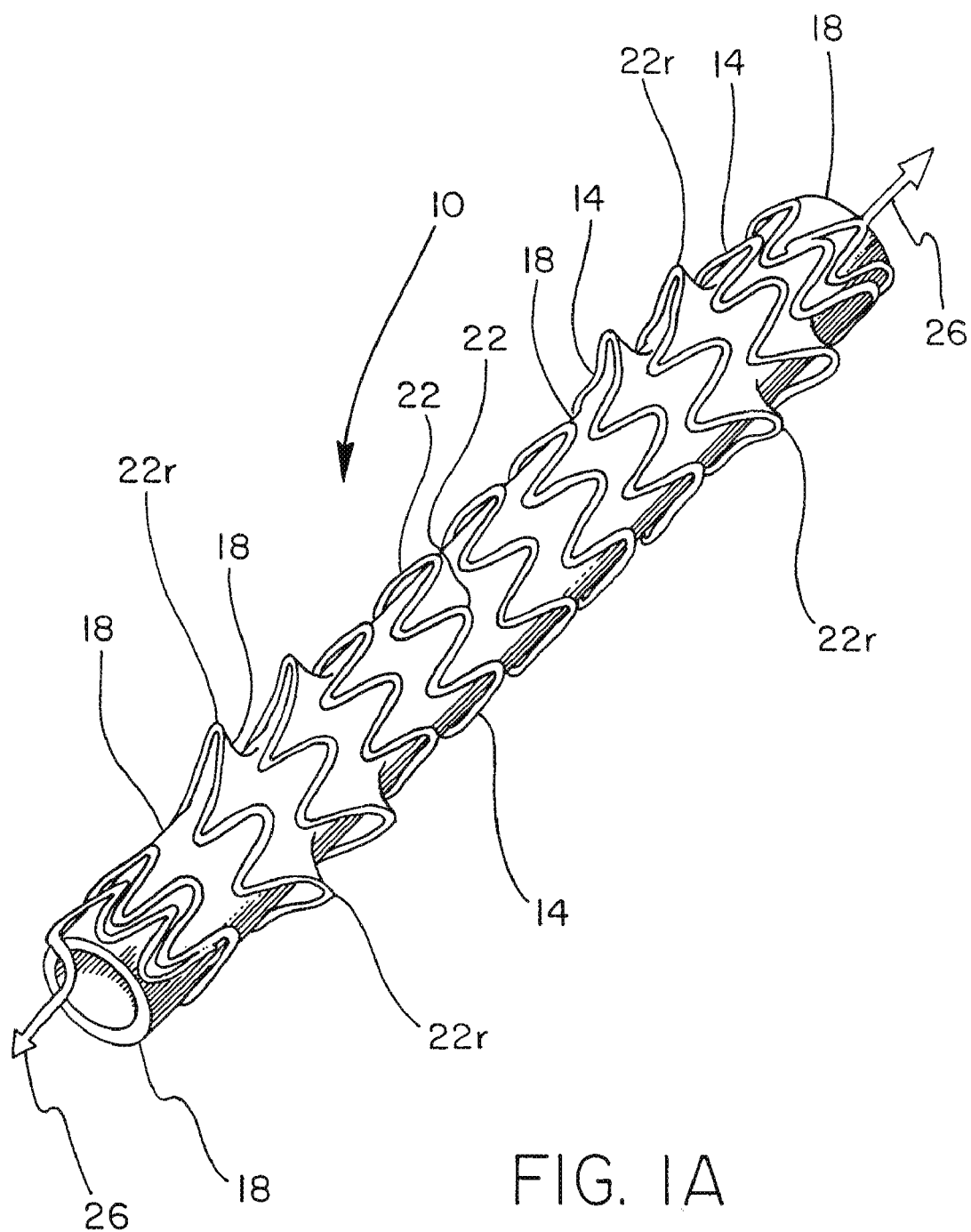

The wire used to fabricate stent component 14 is preferably nitinol wire of, for example, about 0.23 mm diameter. A preferred nitinol wire is wire of this diameter (available from Nitinol Devices & Components Inc., Fremont Calif.) that has been 45% cold worked and electropolished. Most preferably, the stent component is formed from a single length of wire for simplicity and lowest possible profile. One method of forming the wire into the desired serpentine shape is to use a mandrel of similar diameter as the intended diameter of the desired tubular form of the stent-graft. The mandrel is provided with appropriately located pins which protrude radially from the exterior surface of the mandrel in locations corresponding to the intended locations of the apices of the serpentine shape. A suitable length of the wire is then wrapped around the pins protruding from the mandrel surface creating the helically wound serpentine shape that results in the form of stent component 10. Selected pins pertaining to optional raised apices 22r may be placed on appropriately elevated surfaces to achieve the desired amount of elevation. The general form of and method of making such a wire stent are described in WO 97/21403 (see, e.g., FIGS. 1A-2 of WO 97/21403 for the wire form which for purposes of the present invention does not require the additional coupling member 8 or linking member 20). This wire and mandrel assembly may be placed into an oven for any desired heat-treating. Immediately following removal from the oven, the wire and mandrel assembly is quenched in water at about room temperature, following which the formed stent is removed from the mandrel.

FIG. 1 also shows how the adjacent windings (or adjacent elements) of the helically-wound stent component are spaced apart, with the graft material covering the space between the adjacent windings. It is not required that the space between adjacent windings is covered in its entirety by the graft material, although full coverage of these spaces between the adjacent elements of the stent component is generally preferred. The space between adjacent windings or elements of the stent component exists when the stent is in a relaxed state, not subjected to longitudinal compression that could force the adjacent elements to be in contact and therefore no longer spaced apart.

The use of the serpentine winding of stent component 14 shown in FIG. 1 allows the completed stent to be deployed with minimal foreshortening. The stent-graft 10 of the present invention, when deployed from its small, insertion diameter to its largest, fully deployed diameter, will foreshorten less than about 10% of its insertion length. It is also capable of foreshortening less than about 8%, 6%, 4%, 2% or even 0% depending on construction details when properly deployed. Alternatively, if desired, the stent-graft may be made to be controllably foreshortenable during deployment, in significant length amounts, in the interest of making a length-adjustable device. The use of a flexible graft material in conjunction with the arrangement of adjacent apices in the windings of the stent component can allow the device to be controllably shortened in length during deployment, if desired. It can, for example, be controllably foreshortenable by the physician during deployment in an amount equal to about 20% or more of the fully extended length of the device (after being extended by light manually applied axial tension, followed by removal of the tension). It is also possible to provide the device in a form that can be controllably foreshortenable by the physician during deployment in an amount equal to about 50% or more of the fully extended length of the device.

As also shown by FIG. 1, some of the apices 22r of the serpentine-wound wire may be raised above the tubular form so that they protrude somewhat above the outer surface of the remainder of the stent-graft. These protruding or raised apices 22r may be useful as anchoring means for the covered stent 10 in that they will protrude slightly into the wall of any body conduit into which the stent-graft is implanted. In a preferred embodiment for biliary applications, the raised apices 22r are generally located at locations other than at the extreme ends of the stent; they are typically no closer than about 1 mm to the ends of the stent. These raised apices 22r are preferably formed during the forming of the stent wire (preferably nitinol wire and more preferably a single nitinol wire) into the desired serpentine, helically wound shape used for the stent component 14. Further, as shown by the perspective view of FIG. 1A, these raised apices 22r, may optionally be covered with graft material 18 so as to prevent in-growth of tissue into the wire mesh structure (i.e., overgrowth or encapsulation of the apice 22r by living tissue). Prevention of tissue in-growth into the mesh structure would facilitate atraumatic removal of the device 10, even if the device had not been made to be removable by unraveling as described below.

It is apparent that there are a variety of ways of orienting the raised apices to achieve differing desired amounts of anchoring of the deployed stent-graft. Variables include the angle of deviation of apices from parallel to the longitudinal axis of the stent component, the number of raised apices, the height of raised apices, and whether all or any portions of particular apices are raised.

It is generally preferred that raised apices alternate with adjacent apices which are not raised (i.e., adjacent on the same continuous section of stent wire) in the interest of providing a good bond between the stent component and covering graft material. This is particularly true with respect to the embodiment of FIG. 1 and is less critical with regard to the embodiment of FIG. 1A.

Finally, it is apparent that the use of raised apices as described is only one means of providing anchoring for a stent-graft. It is further apparent that, for some applications, anchoring means such as apices may be undesirable.

The attachment of the covering material to the stent component may be accomplished by methods including those described by U.S. Pat. No. 5,735,892 to Myers et al. Mechanical attachment may be by methods such as by the use of sutures. The covering material will preferably be attached to the stent using an adhesive such as, for example, fluorinated ethylene propylene (FEP) which is effective as a meltable thermoplastic adhesive. It is apparent that a variety of adhesives may be used (including thermoset adhesives) as long as the adhesive chosen is adequately biocompatible. The adhesive may be applied to the stent in either solid (powdered) or liquid form by various methods including powder coating, dipping or spraying. Liquid forms may be diluted if desired with appropriate solvents as necessary for the chosen method of application. The adhesive-coated stent component may be heated to ensure uniform coating of the stent component by causing melting of the thermoplastic adhesive.

Alternatively, the coating material applied to the ePTFE film from which the stent covering is made, may also be relied on for joining of the graft material to the stent component.

Figure 2:
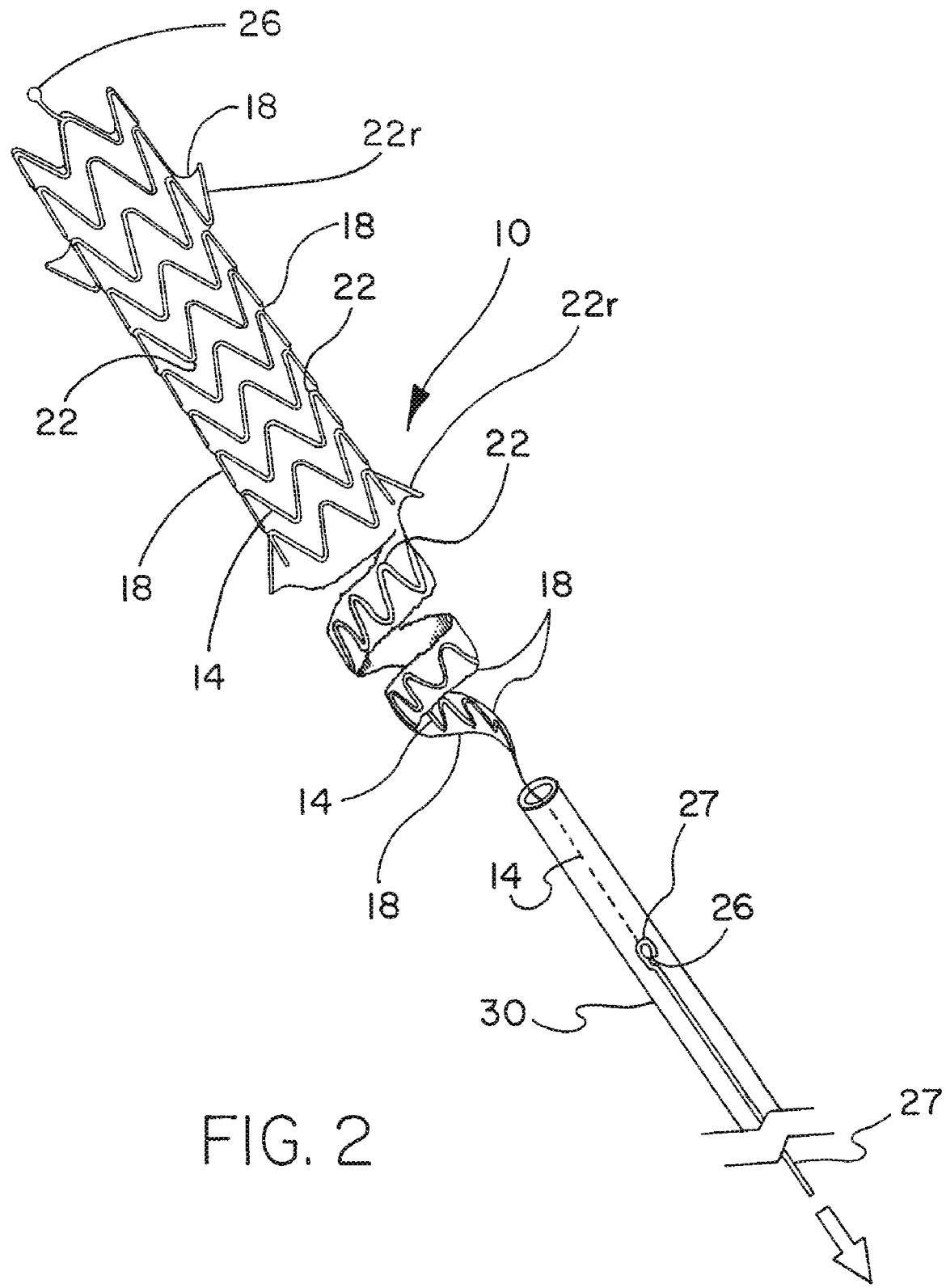
FIG. 2 shows a perspective view of the stent-graft during removal from an implant site by being cohesively disassembled via pulling the end fitting through a retrieval catheter by use of a remotely operated instrument.

FIG. 2 illustrates the device 10 being cohesively disassembled during removal from the body conduit into which it was previously implanted, by means of the end fitting 26 being pulled through a retrieval catheter 30 by use of a remotely operated instrument such as removal tool 27.

As shown, the thin, flexible covering material (graft material 18) is disrupted by the tensile force applied to the stent-graft 10 by the remotely operated instrument 27. As the graft material 18 is disrupted, it remains cohesively attached to the adjacent portion (or element) of stent component 14 which is simultaneously being uncoiled. This disruption, or unraveling, of the graft material 18 and uncoiling of stent component 14, results in minimal trauma to the vessel from which it is being removed as the stent coil diameter is reduced from its expanded state during the disassembling and retrieval process. Further, the graft material 18, attached to the stent component 14, forms into a thin ribbon which fits into a capturing catheter that has been positioned in close proximity to the end of the implanted device 10. This thin ribbon resulting from the unraveling process may have a length that is 100%, 200%, 300%, 400%, 500% or even greater than the length of the deployed stent-graft prior to removal.

The retrieval catheter 30 need only be adequately large diametrically to accommodate the anticipated width of the strip of the stent-graft being removed, i.e., adequately large to accept the substantially straightened serpentine wire form with a small amount of attached graft material. The catheter thus may be smaller in outside diameter than the catheter used previously to initially deliver and implant the device, and likewise smaller than the compacted diameter of the stent-graft itself during delivery to the implantation site (prior to diametrical expansion of the stent-graft during deployment, i.e., the small delivery profile).

Figure 3:
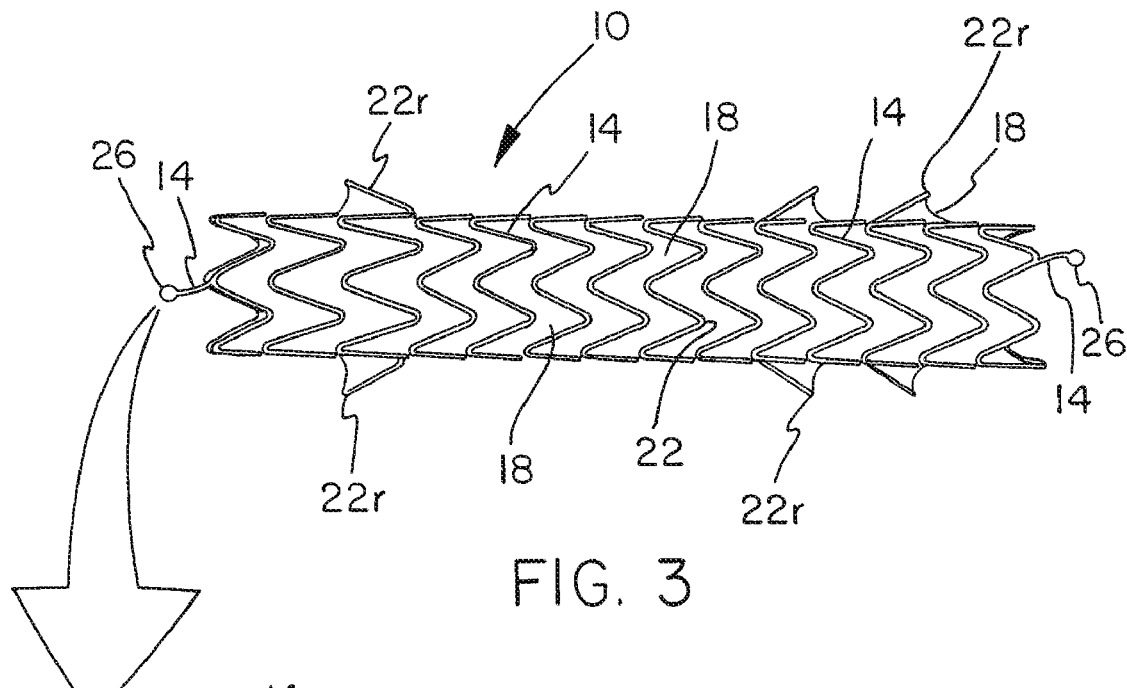
FIGS. 3 and 3A-3D show side views of alternate embodiments of engagement fittings that protrude from either or both ends of the stent-graft.
Figure 3A:
Figure 3B:
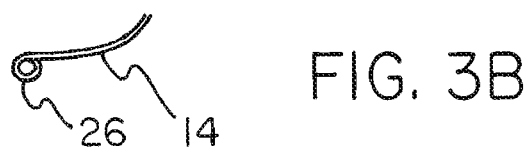
Figure 3C:
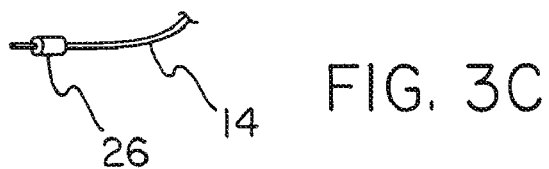
Figure 3D:
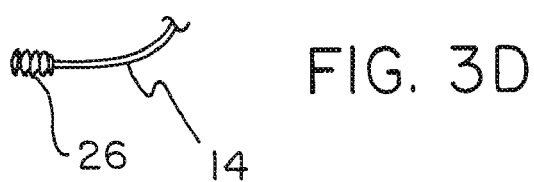

FIGS. 3 and 3A-3D show alternate embodiments of the engagement fittings 26 that protrude from either or both ends of the device 10. These fittings facilitate secure attachment of the ends of the device 10 to an appropriate tool (e.g., removal tool 27) for use in initiating and completing the cohesive disassembly of the device 10. Examples of engagement fittings 26 include a ball as shown in FIG. 3A, a loop as shown in FIG. 3B, a swaged-on end piece as shown in FIG. 3C and a threaded end as shown in FIG. 3D. Other shapes, providing the same function of allowing a removal tool to grasp, attach, or otherwise securely engage onto the fittings 26, could be used as well. It is apparent that the designs of the engagement fitting 26 and removal tool 27 (not shown in FIGS. 3-3D) must be compatible in order to enable the tool 27 to effectively grasp and apply tension to the engagement fitting 26.

Figure 4A:
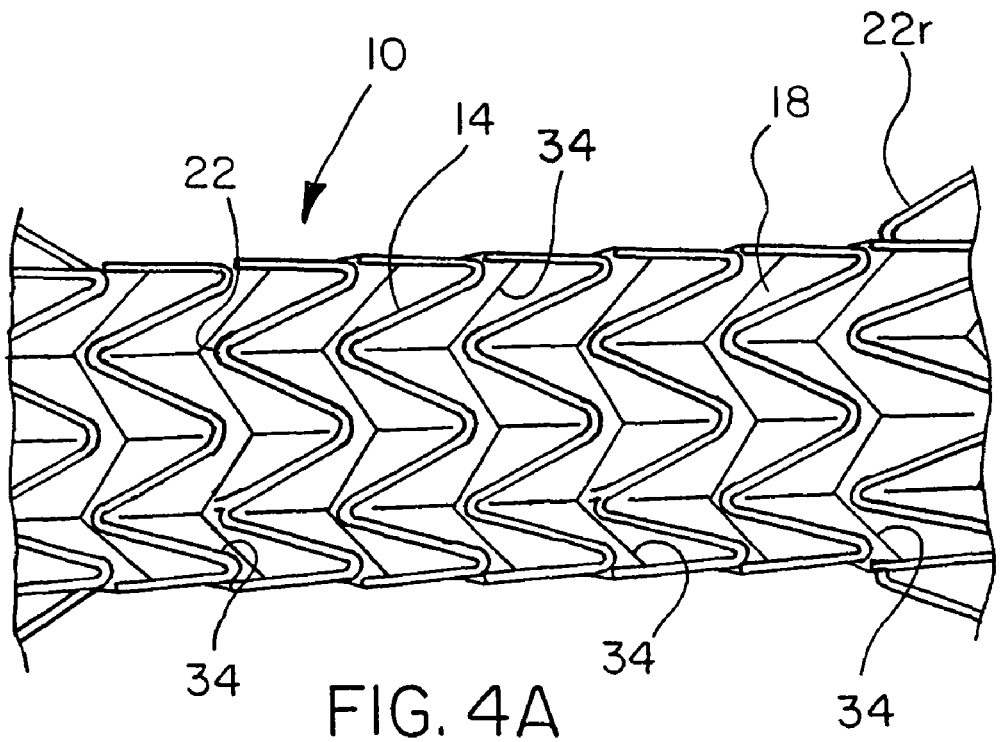
FIGS. 4A-4D show side views of various means of weakening the graft covering material to allow it to separate between adjacent windings of the stent component during removal of the stent-graft.

Numerous means for rendering the graft material 18 able to be cohesively disassembled can be contemplated. FIG. 4A shows a device 10 wherein the graft material 18 is selectively weakened in a prescribed pattern 34. The graft material 18 may be weakened in those areas 34 by mechanical means such as a cutting with a blade or compressing die. Alternatively the graft material 18 may be weakened by use of energy such as with a laser or controlled heating. While the patterns 34 may extend entirely through the wall of the graft material 18, it is preferred that they only extend through a portion of the thickness of the graft material.

Figure 4B:
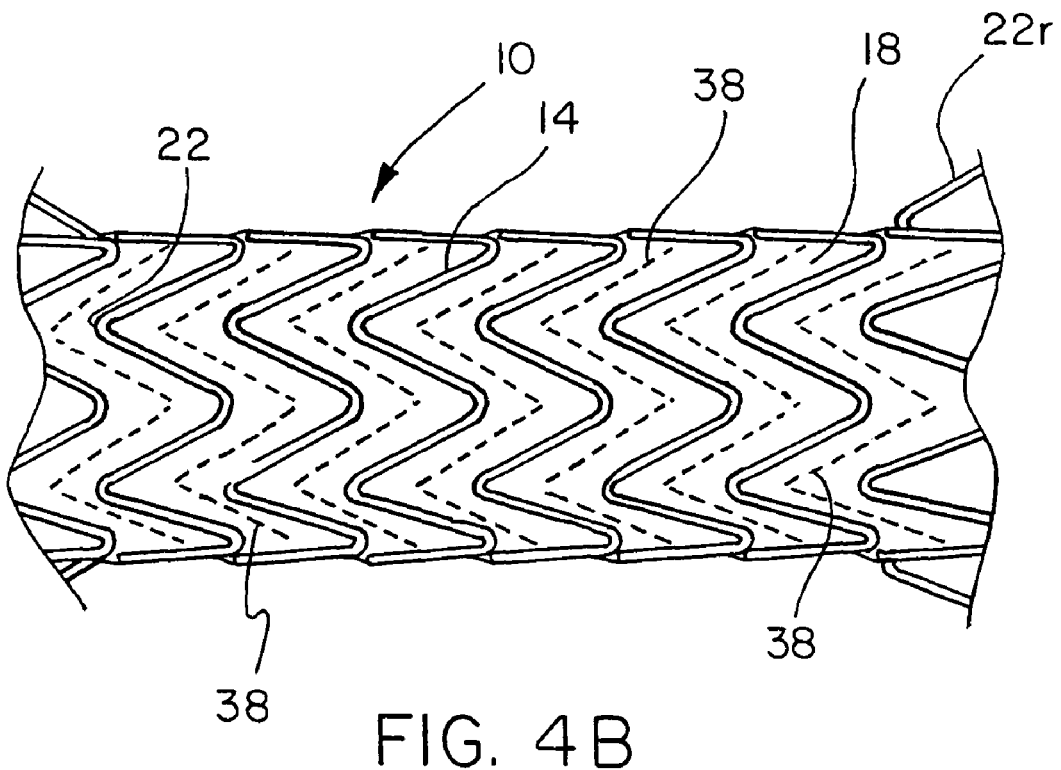

FIG. 4B shows a device 10 wherein the graft material 18 is selectively weakened by perforating the graft material in an alternative prescribed pattern 38. The graft material 18 may be perforated using numerous means, such as with a mechanical cutting blade, a cutting die, a laser, or heat. Perforations 38 may extend entirely through the thickness of the graft material 18, or only extend through a portion of that thickness. When a multi-layer graft material 18 is used, the perforations can be made through one layer, but not through all layers, thereby preventing tissue in-growth through the graft material 18.

Figure 4C:
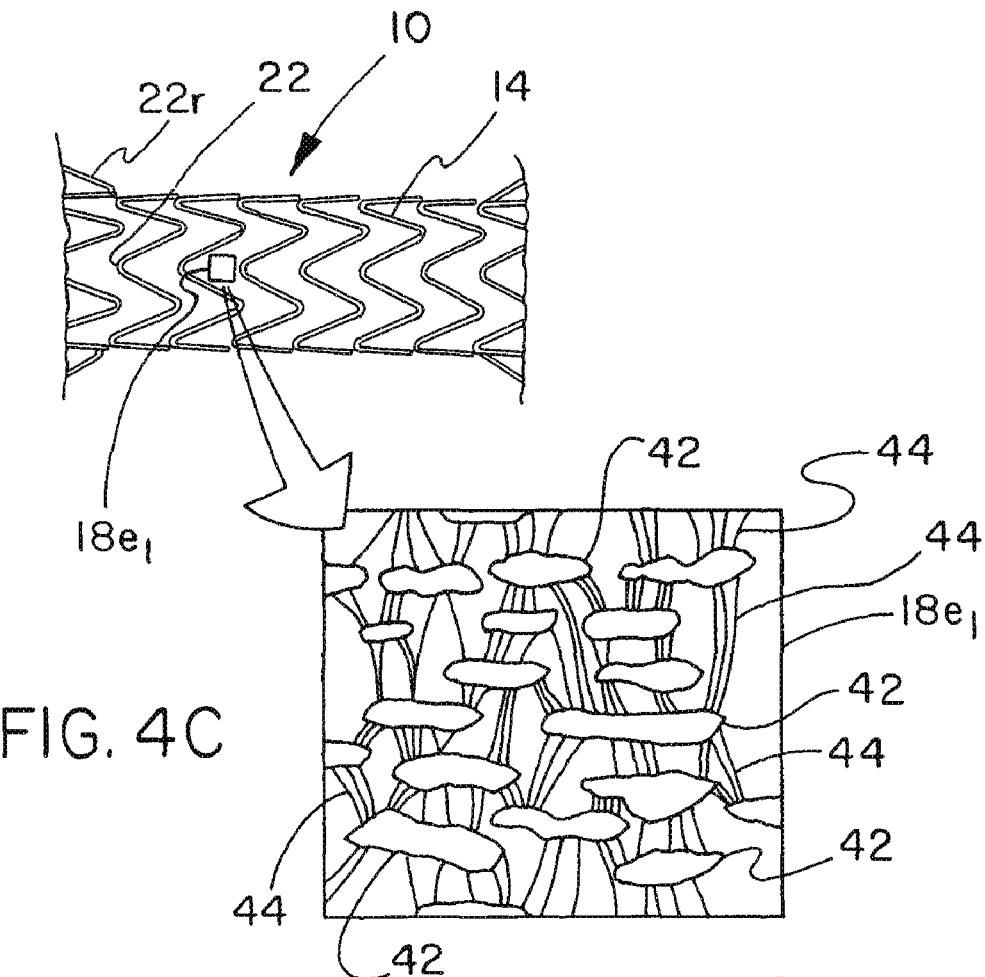

FIG. 4C shows a device 10 wherein a graft material 18 is provided having a node 42 and fibril 44 microstructure (e.g., ePTFE), of which a small sample area 18e, is shown enlarged. This graft material 18 is oriented so as to be weaker in the longitudinal direction than in the radial (circumferential) direction. The ePTFE microstructure shown has a uniaxial microstructure, meaning that the fibrils are oriented primarily in a single direction. The graft material is thus amenable to splitting in the same direction as its direction of greatest strength (i.e., the direction of orientation of the fibrils). This orientation allows for the possibility of the graft material 18 splitting or separating between adjacent windings of the stent component 14 during removal of the stent in the manner previously described (i.e., cohesively disassembling). A preferred method of using such a node and fibril microstructure graft material is to use a film such as an ePTFE film, that has been cut into a long, narrow tape with the length of the tape parallel to the direction of the fibrils. This tape can be used as a graft covering either over or beneath the stent component 14, or both over and beneath stent component 14, and is applied as a helical wrap with the pitch of the helix equal to and parallel to that of the helical pitch of the serpentine stent wire. This allows for disruption of the graft material 18 parallel to the pitch of the serpentine stent winding 14, by splitting of the tape parallel to its length (i.e., parallel to the direction of the fibrils) during stent removal, generally as shown by FIG. 2.

The use of a covering graft material with anisotropic strength properties wherein the graft material is oriented with the direction of greatest strength in the circumferential direction (as described above with the ePTFE film) provides the resulting stent-graft with good hoop strength. Following deployment at a desired site, such a device may be amenable to further expansion using a balloon catheter if it is deemed necessary by the physician.

Figure 4D:
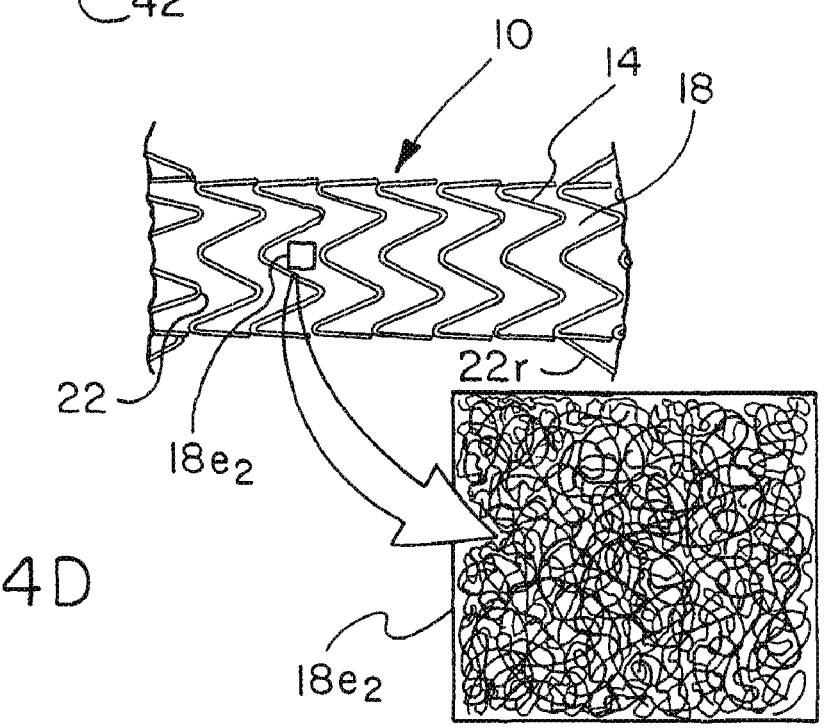

FIG. 4D shows a device 10 wherein the graft material 18 is constructed from a composite of resorbable and non-resorbable materials. The resorbable materials, which may be desirably located in selected areas of the device 10 such as in a line between and parallel to adjacent elements of stent component 14 (similar to the line of perforations 38 of FIG. 4B), are degraded and absorbed by the body. One such resorbable graft material is taught by U.S. Pat. No. 6,165,217 to Hayes; this material takes the form of a fibrous web as shown by the enlargement of $18e_2$. Resorbtion times are typically a function of the resorbable polymer chosen and the thickness of the material. After the resorbable materials have been degraded, weakened areas are formed in the remaining non-absorbable sections of the graft material 18. These weakened areas are more easily disrupted when longitudinal force is applied to an engagement fitting 26, allowing the device 10 to be cohesively disassembled. In addition to the methods described herein, it is apparent that various other methods of selectively weakening the graft material may be contemplated.

Figure 5A:
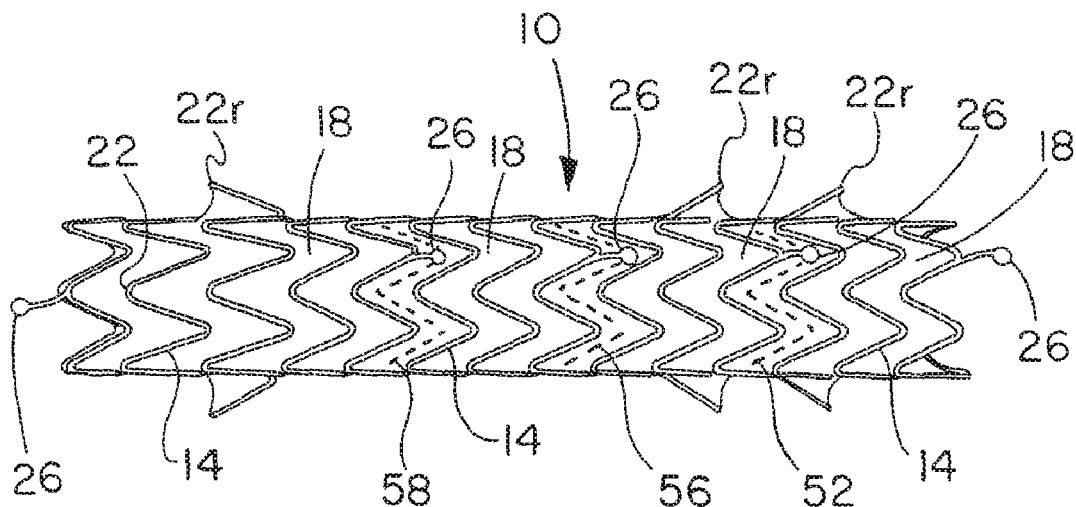
FIGS. 5A-5C illustrate side views of a stent-graft having multiple engagement fittings that coincide with controllably disruptable patterns in the graft material, allowing the graft to be removed in lengthwise segments.
Figure 5B:
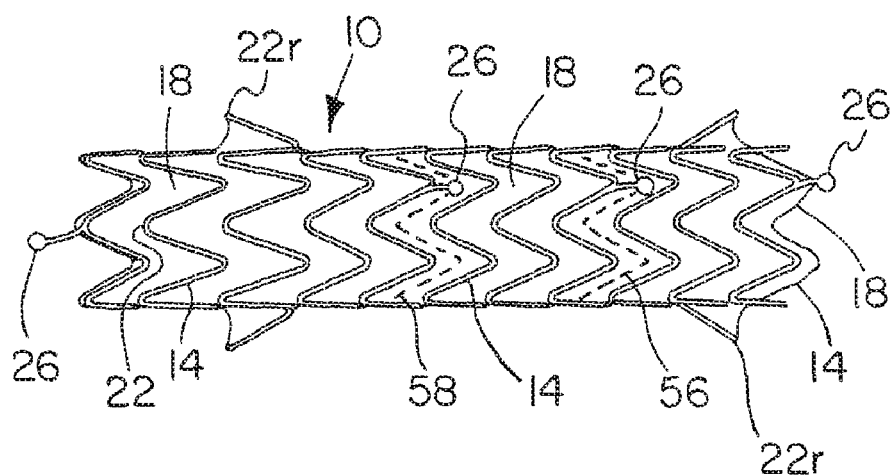
Figure 5C:
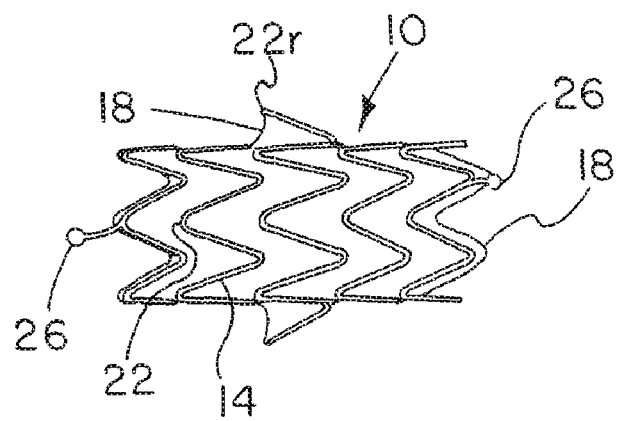

Another embodiment of this invention provides for partial disassembly of the device 10 in situ to allow for shortening of the overall device length, wherein one or more pieces of the device may be cohesively disassembled from the remainder of the stent-graft. FIGS. 5A-5C illustrate a device 10 which has multiple engagement fittings 26, that coincide with controllably disruptable patterns in the graft material 18. The amount of force needed to cause disruption of the graft material 18 and therefore separation of segments of the device 10 can be varied between segments of the device. These disruptable patterns could be arranged so as to have the most easily disrupted pattern 52, closest to the remotely operated removal instrument, with the next most easily disrupted pattern 56, further away from the remotely operated removal instrument. Consistent with this arrangement, the pattern requiring the most force for disruption 58, would be located furthest away from the remotely operated removal instrument. Sequential removal of the segments of the device 10 is described in the sequence shown from FIG. 5A to FIG. 5C, wherein FIG. 5A shows the device as implanted with all three segments. FIG. 5B shows the device 10 after removal of the first segment; FIG. 5C shows the device after removal of the first and second segments. The segments are removed cohesively, meaning that they separate discretely without loss of fragments or pieces. It is apparent that such a device may be provided with a number of segments as desired.

Figure 6A:
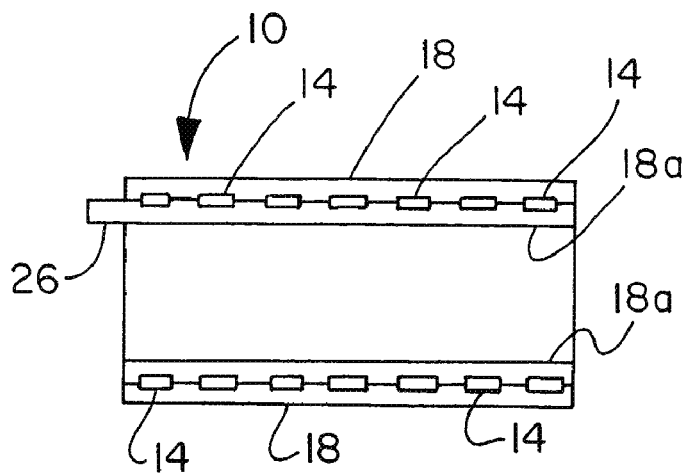
FIGS. 6A-6B show longitudinal cross sections of an alternative embodiment wherein the stent-graft has a luminal liner that is removable at a time subsequent to implantation, while the remainder of the stent-graft is left in place.
Figure 6B:
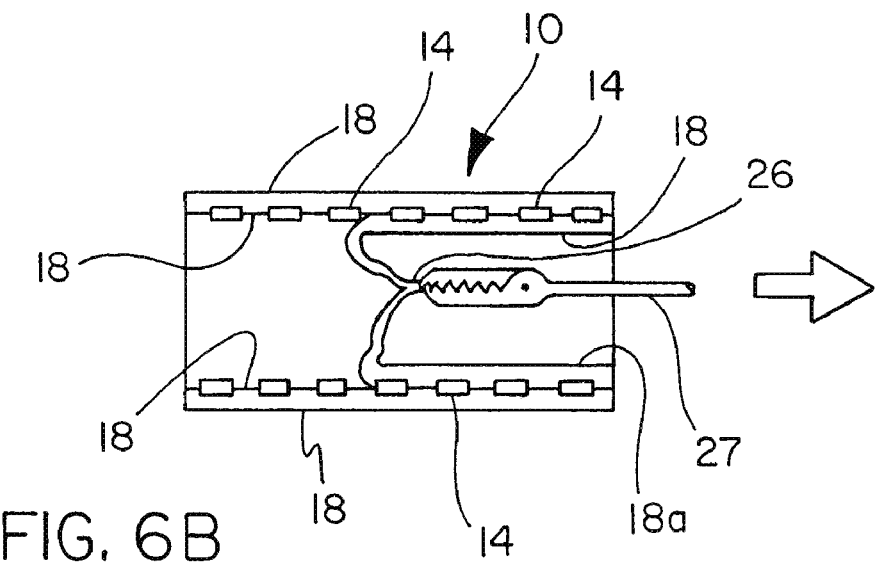

FIGS. 6A-6B show longitudinal cross sections of an alternative embodiment wherein the stent-graft 10 has a luminal liner 18a that is removable at a time subsequent to implantation, while the remainder of the stent-graft 10 is left in place. Liner 18a is provided with a pull-tab or engagement fitting 26 at the distal end of liner 18a. As shown by FIG. 6B, engagement fitting 26 may be grasped by a removal tool 27. The application of tension to engagement fitting 26 via tool 27 allows the liner 18a to be everted and removed through the lumen of stent-graft 10 and the body conduit in which the stent-graft 10 has been previously deployed. This embodiment may be desirable for applications in which, for example, the luminal graft layer 18a has been provided with a drug coating intended for delivery to the site of implantation. It may be desired to subsequently remove layer 18a following a time suitable for the elution of the drug coating. It may also be desirable to have this luminal layer 18a removable to expose the luminal surface of layer 18, which may optionally also be provided with a drug coating of the same drug, or of an entirely different drug.

Figure 7:
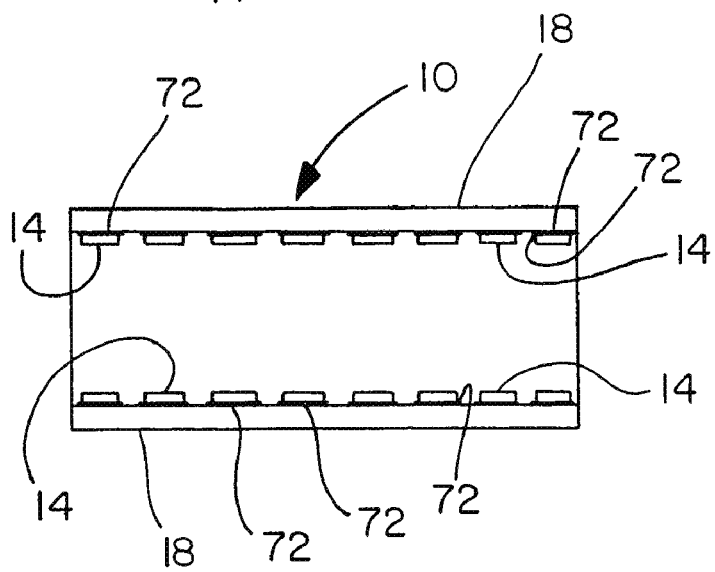
FIG. 7 shows a longitudinal cross section of an alternative embodiment wherein the stent component is secured to the graft material by a resorbable adhesive that allows for removal of the stent component at a time subsequent to insertion and deployment of the stent-graft.

FIG. 7 shows a longitudinal cross section of an alternative embodiment wherein the stent component 14 is secured to the graft material 18 by a resorbable adhesive 72 that allows for removal of the stent component at a time subsequent to insertion and deployment of the stent-graft. The material of the resorbable adhesive may be chosen for a desired time after which the stent component may be removed. This may be useful if, for example, the stent component is intended to deliver a drug to the implantation site and then removed subsequent to elution of the drug coating applied to the stent. Alternatively, it may be desirable to remove stent component 14 after graft material 18 has had adequate time to attach (e.g., via tissue ingrowth) to the luminal surface of the body conduit into which it has been implanted.

Other short-term adhesives are also possible, such as hydrogels (e.g., a 5% solution of polyvinyl alcohol, by weight volume in water). These may be useful, for example, to join together parts of a stent-graft where it may be desired to include components in the construction that are necessary for implantation and deployment, but not needed functionally following deployment. Such components might be longitudinally oriented struts that would ensure that the device is implanted without being twisted. Once deployed, these longitudinally oriented struts could be removed so as not to occupy space within the lumen of the device. These components could be joined to the stent-graft during manufacturing by a temporary adhesive such as a hydrogel, which would be designed to dissolve upon exposure to warm body fluids within a relatively short time such as about 15 minutes, after which they could be removed from within the device. Removal could be accomplished with removal devices as previously described.

Example

A stent component was produced by winding a 0.25 mm diameter nitinol wire (SMA Inc, Santa Clara Calif.) onto an 8 mm diameter wire forming fixture, creating a stent component as shown in FIG. 1. The wire-wound fixture was then subjected to heat treatment and quench cycles sufficient to set the wire into the desired form. FEP powder (Daikin America, Orangeburg N.Y.) was applied to the stent component by first stirring the powder into an airborne "cloud" in a standard kitchen-type blender and suspending the frame in the cloud until a uniform layer of powder was attached to the wire. The stent component was then subjected a thermal treatment of 320° C. for approximately one minute to cause the powder to melt and adhere as a coating over the stent component.

A sacrificial 7 mm inside diameter, 0.1 mm thick ePTFE tube that had been previously heated above 380° C., was pulled onto an 8 mm diameter mandrel, which involved slight stretching of the ePTFE tube. This tube was intended to serve as a release aid when stripping the final construct from the mandrel and would subsequently be discarded.

One layer of a thin ePTFE film provided with a discontinuous coating of FEP was then wrapped around the sacrificial tube. The ePTFE film was of a type produced in accordance with U.S. Pat. No. 5,476,589 to Bacino; it has a greater strength in the longitudinal direction than in the transverse direction. This film was further modified by application of a discontinuous coating of FEP as taught in U.S. Pat. No. 6,159,565 to Campbell et al. The film was applied with the ePTFE side down (toward the mandrel) and with the direction of greater strength oriented circumferentially (i.e., perpendicular to the longitudinal axis of the mandrel). Edges of the film (parallel to the longitudinal axis of the tube and mandrel) were slightly overlapped.

The stent component was carefully fitted over the ePTFE film and tube covered mandrel. Localized heat from a soldering iron was then applied to the wire, causing the FEP wire coating to re-flow and attach to the FEP-coated ePTFE film. When the entire stent component had been joined to the underlying ePTFE film in this manner, one additional layer of the same FEP-coated ePTFE/FEP film is applied over the stent frame. This outer film layer was applied with the FEP side down toward the stent and with the direction of greater strength oriented circumferentially (perpendicular to the longitudinal axis of the mandrel). Longitudinal edges of the film were again slightly overlapped.

The mandrel and construct residing upon it was then subjected to a thermal treatment in an air convection oven set at 320° C. for 5 minutes. After removal from the oven and being allowed to cool to about ambient temperature, the stent-graft was stripped from the mandrel and the sacrificial ePTFE tube was removed from within the stent-graft and discarded. The graft ends were then trimmed as necessary using scissors.

The resulting 8 mm diameter stent-graft was chilled by spraying with Micro Freeze™ (Micro Care Corp., Bristol Conn.) and then diametrically compacted at a temp of −10° C. in a refrigeration chamber. Compaction was effected using a collet or iris type of diametrical compaction device, such as taught by U.S. Pat. No. 6,629,350. The stent-graft was compacted only to a diameter of about 4 mm, adequate to allow it to be inserted into a length of silicone tubing was intended to simulate the lumen of a biliary duct. This silicone tubing (part no. T050PLAT256X236, Jamak Corp., Weatherford Tex.) was of about 6 mm and about 0.25 mm wall thickness. After insertion of the entire length of the stent-graft into the lumen of the silicone tubing, the stent-graft was deployed within the tubing, gripping the luminal surface of the tubing.

The resulting 8 mm diameter stent-graft was demonstrated to be easily and completely removed through the application of a tensile force applied to the device. Removal was effected using a Cordis Brite Tip™ 5 french guide catheter through the proximal end of which had been inserted a length of 0.2 mm diameter nitinol wire that had been doubled back on itself. When the doubled wire was fully inserted, the doubled end of the wire was allowed to extend a short distance beyond the distal tip of the catheter while the two free ends extended from the proximal end. The wire-containing catheter shaft was then inserted into a length of translucent polymer tubing of 2.5 mm inside diameter and 0.035 mm wall thickness. The doubled end of the wire, forming a small loop, was placed over the engagement fitting located at the end of the stent component, after which tension was applied to the wire and catheter assembly by pulling on the proximal end of that assembly with respect to the translucent polymer tube through which it had been inserted. During the application of this tensile force to the stent, the silicone tubing containing the stent was held restrained (resisting the tensile force) in a human hand. The wire-and-catheter assembly was slowly withdrawn in a proximal direction, into the translucent polymer tube. The tensile force, applied to the engagement fitting located at the end of the stent component, caused the stent-graft to unravel and be cleanly withdrawn into the translucent polymer tube, generally as shown by FIG. 2. This tensile force was applied until the entire stent-graft had been withdrawn. Withdrawal was accomplished with minimal distortion or elongation (i.e., minimal trauma) to the silicone tube. No separate remnants of the stent-graft resulted from the removal by unraveling process.

While particular embodiments of the present invention have been illustrated and described herein, the present invention should not be limited to such illustrations and descriptions. It should be apparent that changes and modifications may be incorporated and embodied as part of the present invention within the scope of the following claims.

We claim:

1. An endoprosthesis comprising:
   a stent component having opposing ends and further having a reduced delivery profile and an enlarged deployed profile;
   said stent component comprising a wire formed into a helical winding having space between adjacent elements of the helical winding, wherein the helical winding provides a tubular form to the stent component and wherein the helical winding includes at least one apex located between the opposing ends of the stent component;
   a graft material attached to the stent component covering the space between each adjacent element of the helical winding, wherein the graft material provides a continuous luminal surface between the opposing ends of the stent component; and
   wherein at least one of said apices located between the opposing ends of the stent component is raised to protrude outwardly from said tubular form and wherein the resulting raised apex is covered by said graft material.

2. The endoprosthesis of claim 1 wherein following deployment, the endoprosthesis is adapted to be cohesively disassembled to allow for its remote removal from a patient.

3. The endoprosthesis of claim 1 wherein at least a portion of the helical winding has a serpentine form with alternating opposing apices.

4. The endoprosthesis of claim 3 wherein following deployment, the endoprosthesis is adapted to be cohesively disassembled to allow for its remote removal from a patient.

5. The endoprosthesis of claim 1 wherein said graft material is impermeable to body fluids.

6. The endoprosthesis of claim 1 wherein said graft material is ePTFE.

7. The endoprosthesis of claim 6 wherein said graft material is ePTFE provided with a coating of FEP.

8. An endoprosthesis comprising:
   a stent component having opposing ends and further having a reduced delivery profile and an enlarged deployed profile;
   said stent component comprising helically arranged structural elements and space between adjacent structural elements, wherein the structural elements provide a tubular form to the stent component and wherein the structural elements include at least one apex located between the opposing ends of the stent component;
   a graft material attached to the stent component covering the space between each adjacent structural element, wherein the graft material provides a continuous luminal surface between the opposing ends of the stent component; and wherein at least one of said apices located between the opposing ends of the stent component is raised to protrude outwardly from said tubular form and wherein the resulting raised apex is covered by said graft material whereby encapsulation of the raised apex by living tissue is prevented.

9. The endoprosthesis of claim 8 wherein following deployment, the endoprosthesis is adapted to be cohesively disassembled to allow for its remote removal from a patient.

10. The endoprosthesis of claim 8 wherein at least a portion of the stent component has a serpentine form with alternating opposing apices.

11. The endoprosthesis of claim 10 wherein following deployment, the endoprosthesis is adapted to be cohesively disassembled to allow for its remote removal from a patient.

12. The endoprosthesis of claim 8 wherein said graft material is impermeable to body fluids.

13. The endoprosthesis of claim 8 wherein said graft material is ePTFE.

14. The endoprosthesis of claim 13 wherein said graft material is ePTFE provided with a coating of FEP.

* * * * *